United States Patent [19]

Shudo et al.

[11] Patent Number: 5,525,618
[45] Date of Patent: Jun. 11, 1996

[54] METHOD OF TREATING BONE DISEASE WITH PYRIDINE, CARBOXAMIDE AND CARBOXYLIC DERIVATIVES

[75] Inventors: Koichi Shudo, Tokyo; Tatsuo Sugioka, Saitama; Mizuho Inazu, Iruma; Hideyuki Tanaka, Kawagoe; Tsutomu Inoue, Hidaka; Kazuyuki Kitamura, Sakado, all of Japan

[73] Assignee: Hoechst Japan Limited, Japan

[21] Appl. No.: 221,600

[22] Filed: Apr. 1, 1994

[30] Foreign Application Priority Data

Apr. 5, 1993 [JP] Japan ................................. 5-078320

[51] Int. Cl.⁶ .................... A61K 31/44; A61K 31/195; A61K 31/24
[52] U.S. Cl. .................... 514/352; 514/563; 514/535; 514/539
[58] Field of Search .................... 514/352, 563, 514/535, 539

[56] References Cited

U.S. PATENT DOCUMENTS 5,070,108 12/1991 Margolis.

OTHER PUBLICATIONS

Chemical Abstracts; vol. 108, No. 37406m, Shroot et al (1988).
Pharmaceutical Sciences (1980), MACK Publishing Co. pp. 420–427.
Tamura et al., "Synthetic Retinoids, Retinobenzoic Acids, Am80, Am580 and Ch55 Regulate Morphogenesis in Chick Limb Bud," Cell Differentiation and Development, vol. 32, 1990, pp. 17–26.
Mark et al., "Effects of Retinoids on Tooth Morphogenesis and Cytodifferentiations, in vitro," Int. J. Dev. Biol. vol. 36, 1992, pp. 517–526.
Oikawa et al., "Three Novel Synthetic Retinoids, Re 80, Am 580 and Am 80, All Exhibit Anti-Angiogenic Activity In Vivo," European Journal of Pharmacology, vol. 249, 1993, pp. 113–116.
Gianni et al., "Effects of Synthesis Retinoids and Retinoic Acid Isomers on the Expression of Alkaline Phosphatase in F9 Teratocarcinoma Cells," Biochemical and Biophysical Research Communications, vol. 196, No. 1, 1993, pp. 253–259.
R. P. J. O'Neill et al., "Effect of Retinoic Acid on the Resorptive Activity of Chick Osteoclasts In Vitro," Bone, 13, pp. 23–27 (1992).
H. Gollnick et al., "Retinoids: An Overview of Pharmacokinetics and Therapeutic Value," Methods in Enzymology, vol. 190, pp. 291–304, (1990).

*Primary Examiner*—Theodore J. Criares
*Attorney, Agent, or Firm*—Finnegan, Henderson, Farabow, Garrett & Dunner

[57] ABSTRACT

Treatment of osteopathic comprising administering as an active ingredient a compound represented by the following formula (I), (II) or (III):

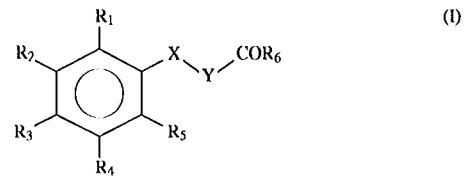

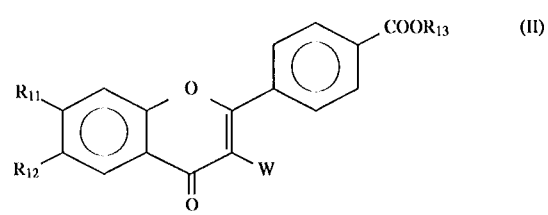

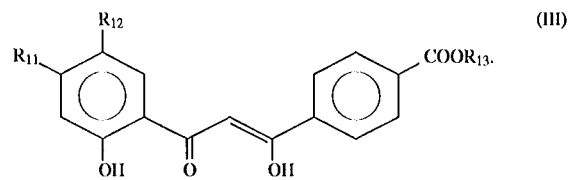

1 Claim, No Drawings

METHOD OF TREATING BONE DISEASE WITH PYRIDINE, CARBOXAMIDE AND CARBOXYLIC DERIVATIVES

The present invention relates to an anti-osteopathic composition useful for therapeutic and prophylactic treatment of osteopathic. More specifically, the present invention relates to an anti-osteopathic composition comprising an aromatic carboxylic acid or its derivative as an active ingredient. The anti-osteopathic composition can be used for, for example, a therapeutic and prophylactic treatment of osteodysbolism or a therapeutic and prophylactic treatment of fractures.

Metabolism of bones is considered to be achieved by well balanced repetitions of bone resorption by osteoclasts and osteogenesis by osteoblasts. Dynamic equilibrium is maintained between such generation process and resorption process in healthy adults and, as a result, weights and structures of their bones are maintained. It is suggested that main cause of various osteodysbolisms, including osteoporosis as an typical example, is an abnormal mutual cooperation of these two processes.

Osteoporosis is a disease in which reductions of bone densities and bone amounts are brought about as a result of excess bone resorptions which are induced by a lost of the aforementioned balance with an increased bone resorption. This disease outbreaks in adults and is frequently observed particularly in women of middle and advanced age. Patients of this disease are susceptible to fractures because of the reductions of bone density and amount, and some patients fall into serious conditions, such as conditions where they are entirely in beds. Therefore, development of therapeutic drugs effective for osteoporosis is being highly desired.

As medicaments for the treatment of such osteopathic, compositions such as, for example, those comprising activated-form vitamin $D_3$, calcitonin, bis-phosphonic acid, estrogen, ipriflavone, and calcium are used. Most of these pharmaceutical compositions are reported to have inhibitory activity on bone resorption or the like. However, it has not been clearly demonstrated that these compositions have enhancing activities on osteogenesis.

Vitamin A acid (retinoic acid), an oxidative metabolite of vitamin A (retinol), has been reported to have therapeutic efficacy on certain types of leukemia, skin cancer and intractable skin diseases, in addition to its pharmacological activities relating to life sustainment, embryogenesis and growth of animals. Among retinoids (a generic term for compounds exhibiting retinoic acid-type biological activities) having various pharmacological activities, isotretinoin and etretinate having a polyene structure similar to that of retinoic acid are practically used as clinical medicaments. They are mainly used as medicaments for the therapeutic treatment of intractable skin diseases.

So far, some experimental results in vitro with respect to an activity of retinoic acid on osteocytes have been reported (R. P. J. Oncill et al., Bone, Vol. 13, pp. 29–47, 1992). However, effects of retinoic acid on osteocytes have been remained unclear because contrary results have been also reported. Furthermore, etretinate, one of synthetic retinoids, has been known to induce a clinical side effect of hyperostosis (Methods in Enzymology, Vol. 190, pp. 291–304, 1990, Academic Press). U.S. Pat. No. 5,070,108 discloses a method of using etretinate for the treatment of osteoporosis. However, retinoic acid, retinol, retinal, etretinate, isotretinoin and the like are not sufficiently effective as medicament for the treatment of osteopathic, in particular, osteoporosis, since they are unstable due to their polyene structures, and moreover, they have various kinds of pharmacological activities.

Therefore, an object of the present invention is to provide retinoid compounds which successfully enhance osteogenesis at low concentrations with high specificity for osteogenesis enhancing activity and are chemically stable. The inventors of the present invention conducted various studies to achieve the foregoing object, and as a result, they found that aromatic carboxylic acids and their derivatives set out below are effective for therapeutic and prophylactic treatment of osteopathia. The present invention was achieved on the basis of these findings. In the specification, the term "osteopathia" means all sorts of diseases relating to bones such as, for example, bone metabolic disorders and bone fractures. The anti-osteopathic composition of the present invention can be used for therapeutic and prophylactic treatment of osteopathia such as, for example, osteoporosis and bone fracture.

The present invention thus provides an anti-osteopathic composition comprising as an active ingredient a compound represented by the following formula (I):

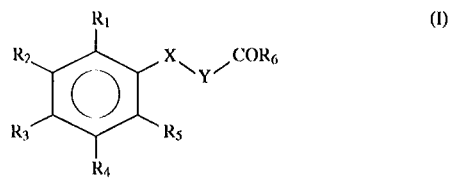

wherein $R_1$, $R_2$, $R_3$, $R_4$ and $R_5$ independently represent a hydrogen atom, a lower or middle alkyl group, or a lower or middle alkoxy group, with the proviso that all of $R_1$, $R_2$, $R_3$, $R_4$ and $R_5$ do not simultaneously represent hydrogen atoms, any two adjacent groups selected from these groups may combine to form a 5- or 6-membered cycloalkyl ring together with carbon atoms substituted by those groups and the cycloalkyl ring may further be substituted with one or more lower alkyl groups; $R_6$ represents a hydroxyl group, a lower alkoxy group, or $-NR_7R_8$ group in which $R_7$ and $R_8$ independently represent a hydrogen atom or a lower alkyl group; X represents a radical selected from the group consisting of the radicals represented by the following formulas:

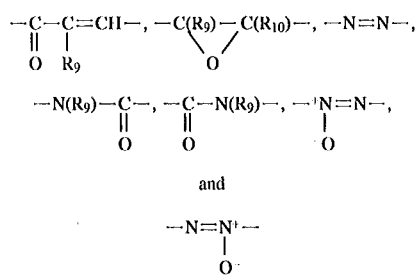

and $$-N=N^+-$$
$$\phantom{-N=N^+}\,|$$
$$\phantom{-N=N^+}O^-$$

wherein $R_9$ and $R_{10}$ independently represents a hydrogen atom or a lower alkyl group and; Y represents a radical selected from the group consisting of the radicals represented by the following formulas:

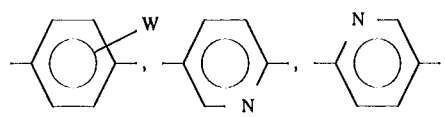

wherein W represents a hydrogen atom or a hydroxy group, or a salt of said compound.

According to the present invention, there is further provided an anti-osteopathic composition comprising as an active ingredient a compound represented by the following formula (II) or (III):

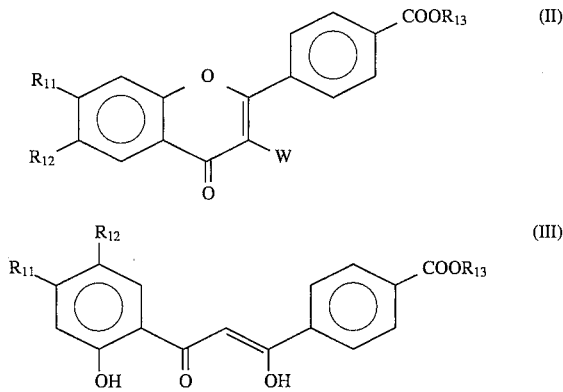

wherein $R_{11}$ and $R_{12}$ independently represent a hydrogen atom or a lower or middle alkyl group or $R_{11}$ and $R_{12}$ may combine to form a 6-membered cycloalkyl ring together with carbon atoms substituted by these groups and said cycloalkyl ring may contain an oxygen atom and may be substituted by one or more lower alkyl groups; $R_{13}$ represents a hydrogen atom or a lower alkyl group; and W represents a hydrogen atom or a hydroxy group, or a salt of said compound.

Specific examples of the carboxylic acids and their derivatives according to the present invention represented by the aforementioned formula (I) include the following compounds, but the present invention is not limited to these compounds:

4-[(5,6,7,8-tetrahydro-5,5,8,8-tetramethyl-2-naphthalenyl)carboxamide]benzoic acid (hereinafter referred to as "Am580");

4-[(3,4-diisopropylphenyl)carboxamide]benzoic acid;

5-[(5,6,7,8-tetrahydro-5,5,8,8-tetramethyl-2-naphthalenyl)carboxamide]pyridine-2-carboxylic acid;

6-[(5,6,7,8-tetrahydro-5,5,8,8-tetramethyl-2-naphthalenyl)carboxamide]pyridine-3-carboxylic acid;

3-hydroxy-4-[(5,6,7,8-tetrahydro-5,5,8,8-tetramethyl-2-naphthalenyl)carboxamide]benzoic acid (hereinafter referred to as "Am589");

4-[(3-isopropyl-4-isopropoxyphenyl)carboxamide]benzoic acid (hereinafter referred to as "Am685");

3-hydroxy-4-[(3-isopropyl-4-isopropoxyphenyl)carboxamide]-benzoic acid (hereinafter referred to as "Am689");

4-[(5,6,7,8-tetrahydro-5,5,8,8-tetramethyl-2-naphthalenyl)carbamoyl]benzoic acid (hereinafter referred to as "Am80");

4-[(3,4-diisopropylphenyl)carbamoyl]benzoic acid;

5-[(5,6,7,8-tetrahydro-5,5,8,8-tetramethyl-2-naphthalenyl)carbamoyl]pyridine-2 -carboxylic acid;

(E)-4-[3-(3,5-di-tert-butylphenyl)-3-oxo-1-propenyl]benzoic acid (hereinafter referred to as "Ch55");

(E)-4-[3-(3,5-diisopropylphenyl)-3-oxo-1-propenyl]benzoic acid;

6-[(5,6,7,8-tetrahydro-5,5,8,8-tetramethyl-2-naphthalenyl)carbamoyl]pyridine-3 -carboxylic acid (hereinafter referred to as "R300");

4-[3-methyl-3-(5,6,7,8-tetrahydro-5,5,8,8-tetramethyl-2-naphthalenyl)oxylanyl]-benzoic acid;

4-[(5,6,7,8-tetrahydro-5,5,8,8-tetramethyl-2-naphthalenyl)azoxy]benzoic acid;

4-[(5,6,7,8-tetrahydro-5,5,8,8-tetramethyl-2-naphthalenyl)azo]benzoic acid;

4-[(3,5-di-tert-butylphenyl)carboxamide]benzoic acid;

4-[(3,5-di-tert-butylphenyl)carbamoyl]benzoic acid;

5-[(3,4-diisopropylphenyl)carboxamide]pyridine-2-carboxylic acid;

6-[(3,4-diisopropylphenyl)carboxamide]pyridine-3-carboxylic acid;

5-[(3,4-diisopropylphenyl)carbamoyl]pyridine-2-carboxylic acid;

6-[(3,4-diisopropylphenyl)carbamoyl]pyridine-3-carboxylic acid;

4-[3-(5,6,7,8-tetrahydro-5,5,8,8-tetramethyl-2-naphthalenyl)-oxyranyl]benzoic acid (hereinafter referred to as "Ep80"); and 4-[(3,4-diisopropylphenyl)azo]benzoic acid (hereinafter referred to as "Az68").

Examples of the compounds represented by the formula (II) include 4-(6,7,8,9-tetrahydro-3-hydroxy-6,6,9,9-tetramethyl-4H-4-oxonaphtho[2,3-b]-pyran-2-yl)benzoic acid (hereinafter referred to as "Fv180") and 4-(6,7,8,9-tetrahydro-6,6,9,9-tetramethyl-4H-4-oxonaphtho[2,3-b]pyran-2-yl)-benzoic acid (hereinafter referred to as "Fv80"); and examples of the compounds represented by the formula (III) include 4-[1-hydroxy-3-oxo-3-(5,6,7,8-tetrahydro-3-hydroxy-5,5,8,8-tetramethyl-2 -naphthalenyl)-1-propenyl]benzoic acid (hereinafter referred to as "Re80"), but the present invention is not limited to these compounds.

The term "lower or middle alkyl group" herein used means an alkyl group having 1 to 4 carbon atoms such as methyl, ethyl, isopropyl, n-propyl, n-butyl, iso-butyl and tert-butyl, and "lower alkyl" means methyl or ethyl group. The term "lower or middle alkoxy group" means an alkoxy group having 1 to 4 carbon atoms such as methoxy, ethoxy, isopropoxy, n-propoxy, n-butoxy, iso-butoxy and tert-butoxy.

The aforementioned compounds contained in the anti-osteopathic composition of the present invention can be prepared, for example, according to methods described in Japanese Patent Unexamined Publication Nos. (Sho) 61-22047, (Sho) 61-76440, (Sho) 62-190154, and (Sho) 62-215581, and Japanese Patent Application No. (Hei) 3-328633. However, the methods for preparing the aforementioned compounds are not limited to these methods. For example, synthetic intermediates for the preparation of these compounds can be prepared according to a method described in the Journal of Antibiotic, Vol. 21, No. 10, pp. 603–610, 1968.

The anti-osteopathic composition of the present invention comprises, as an active ingredient, the compounds described above in the form of a free compound or a pharmaceutically acceptable salt. Examples of the pharmaceutically acceptable salt include, for example, sodium, potassium, calcium, ammonium and amine salts. The anti-osteopathic composition of the present invention may comprise two or more of the compounds described above in any combination thereof. Furthermore, it may comprises medicaments for the treatment of osteopathia such as, for example, vitamin D and calcium and other therapeutically active ingredients.

The aforementioned compounds contained in the anti-osteopathic composition of the present invention have potent osteogenesis enhancing activities. When used as medicaments for the treatment of osteopathia, e.g., osteoporosis, the present compounds exhibit remarkable effects on the enhancement of osteogenesis. They may also be used for preventing bone fractures, and furthermore, they may be used as medicaments for the treatment of bone fractures where healing processes necessarily include osteogenesis.

Route of administration of the anti-osteopathic composition of the present invention is not particularly limited, and the composition may be administered orally or parenterally. For example, pharmaceutical formulations suitable for oral administration include, for example, tablets, capsules, powders, subtilized granules, granules, liquid compositions and syrups. Pharmaceutical formulations suitable for parenteral administration include, for example, injections, suppositories, inhalants, ointments, plasters, and implants. The anti-osteopathic composition of the present invention may be prepared using pharmacologically and pharmaceutically acceptable additives, if desired. Examples of the pharmacologically and pharmaceutically acceptable additives include, for example, excipients, disintegrating agents or disintegrators, binders, lubricants, coating agents, colorants, diluents, bases, dissolving agents or solubilizer, isotonizing agents, pH adjusting agents, stabilizers, propellants, and thickening agents.

The pharmaceutical formulations suitable for oral, percutaneous or permucosal administration can be added with pharmaceutical additives such as, for example, an excipient such as glucose, lactose, D-mannitol, starch and crystalline cellulose; a disintegrating agent or a disintegrator such as carboxymethylcellulose, starch, and calcium carboxymethylcellulose; a binder such as hydroxypropylcellulose, hydroxypropylmethylcellulose, polyvinylpyrrolidone, and gelatin; a lubricant such as magnesium stearate, and talc; a coating agent such as hydroxypropylmethyl-cellulose, saccharose, polyethylene glycol, and titanium oxide; a base such as petrolatum, liquid paraffin, polyethylene glycol, gelatin, kaolin, glycerine, purified water, and hard fat; a propellant such as flon, diethyl ether and pressured gas; a thickening agent such as sodium polyacrylate, polyvinyl alcohol, methylcellulose, polyisobutylene and polybutene; and a base sheet such as cotton fabric and plastic sheet. The pharmaceutical formulations suitable for injection can be added with pharmaceutical additives such as, for example, a dissolving agent or a solubilizer such as distilled water, physiologic saline, and propylene glycol which can be comprised of an aqueous injections or an injection to be dissolved upon using; an isotonizing agent such as glucose, sodium chloride, D-mannitol, and glycerine; a pH adjusting agent such as inorganic acids, organic acids, inorganic bases, and organic bases. Furthermore, the pharmaceutical preparation may be administered as an implant at a site of a bone fracture to enhance an effect of the treatment of the fracture.

The dose of administration of the anti-osteopathic composition of the present invention is not particularly limited, and the dose may suitably be choosen depending on the route of administration, age, body weight, and condition of a patient. For example, where the composition is administered orally, it can be administered to an adult patient in an amount of 0.05 to 100 mg, preferably, 0.1 to 50 mg per day. The anti-osteopathic composition of the present invention may be administered once or several times a day. In addition, a period of time for administration may also suitably be choosen depending on age, condition of a patient and the like.

The osteogenesis enhancing activities of the compounds contained in the anti-osteopathic composition of the present invention has been demonstrated by an in vitro experiment in which their alkaline-phosphatase activities were studied by using an osteoblast-like mouse cell-line MC3T3-E1 (H. Kodama et al., Jpn. J. Oral. Biol., Vol. 23, p.899–901, 1981). Efficacy of the compounds in vivo was also revealed by examining their activities on rat bone atrophy which was experimentally induced by immobilization.

More specifically, during a course of experiments in vitro in which effects on an activity of alkaline phosphatase, a marker enzyme of osteoblast having osteogenetic functions and is generally reported to contribute to a calcification of calcium, i.e., an activation of osteogenesis, it was found that the aforementioned compounds activate osteogenesis of osteoblasts. In addition, an animal model was used as an experimental system in vivo in which bone atrophy was induced by neurectomy in a rat fore-leg to cause immobilization of the fore-leg. This model system has been widely used for developments of medicaments for therapeutic treatments of osteopathia including osteoporosis. It was demonstrated that the aforementioned compounds exhibit remarkable efficacy in this model system.

EXAMPLES

The present invention will be further explained hereinafter by way of examples, but the scope of the present invention is not limited to these examples.

Preparation of novel compounds contained in the anti-osteopathic composition of the present invention are specifically explained by way of preparation examples set out below.

PREPARATION EXAMPLE 1

(i) To a mixture of acetic anhydride (37.8 g) and pyridine (40.1 g), o-isopropylphenol (10.7 g) was added at 0° C., and then the mixture was stirred for 2 hours at room temperature. After a completion of the reaction, the reaction mixture was poured into ice-water, and the mixture was extracted with ethyl acetate. The organic layer was concentrated under reduced pressure, and the residue was purified by column chromatography using silica gel (n-hexane: ethyl acetate= 30:1) to give o-isopropylphenylacetate (13.3 g) as an oil.

(ii) To a mixture of the compound obtained in the above step (i) (13.3 g) and nitrobenzene (70 ml), aluminium trichloride (14.0 g) was added fourfold portionwise, and then the mixture was stirred at room temperature for 24 hours. The reaction mixture was poured into an aqueous hydrochloric acid, and the mixture was extracted with ethyl acetate. Ethyl acetate and nitrobenzene were evaporated under reduced pressure, and the resulting crystals were washed with n-hexane to give 3-isopropyl-4-hydroxyacetophenone (10.0 g).

(iii) A mixture of the compound obtained in the above step (ii) (4.9 g), potassium carbonate (15.1 g), isopropylbromide (6.9 g), and dry acetone (100 ml) was stirred under reflux for 24 hours. After a completion of the reaction, the reaction mixture was poured into ice-water, and then the mixture was extracted with ethyl acetate. The organic layer was concentrated under reduced pressure, and the residue was purified by column chromatography using silica gel (n-hexane: ethyl acetate=3:2) to give 3-isopropyl-4-isopropoxyacetophenone (5.5 g) as an oil.

(iv) A mixture of chlorinated lime (12.5 g), potassium carbonate (8.6 g), potassium hydroxide (2.5 g), and water (45 ml) was vigorously stirred for 30 minutes at 60°–70° C., and then the mixture was filtered. The compound obtained in the above step (iii) (5.5 g) was added to the filtrate, and then the mixture was stirred for 5 hours at 50°–60° C. After a completion of the reaction, the reaction mixture was extracted with ether to remove by-products. The aqueous layer was adjusted to pH 1 and extracted with ether. The organic layer was concentrated under reduced pressure to give crude crystals. The crystals were washed with n-hexane to afford 3-isopropyl-4-isopropoxybenzoic acid (3.7 g).

(v) To the compound obtained in the above step (iv)(1.8 g), thionyl chloride (10 ml) and dimethylformamide (2 drops) were added, and then the mixture was stirred at 3 hours at room temperature. The reaction mixture was concentrated to dryness under reduced pressure to remove an excess thionyl chloride. Pyridine (15 ml), ethyl p-aminobenzoate (1.4 g), and dimethylaminopyridine (100 mg) were added to the residue and then the mixture was stirred for 3 hours at room temperature. After a completion of the reaction, the reaction mixture was poured into ice-water, and the mixture was extracted with ethyl acetate. The organic layer was concentrated under reduced pressure, and the resulting residue was purified by column chromatography using silica gel (chloroform:methanol=30:1) to give an ester compound (2.5 g). Ethanol (20 ml) and 4N aqueous sodium hydroxide solution (8 ml) was added to the ester, and the mixture was stirred for 6 hours at about 50° C. After a completion of the reaction, the reaction mixture was concentrated under reduced pressure. Water was added to the residue and the mixture was acidified using an aqueous hydrochloric acid to obtain crude crystals. The crystals were washed with a mixture of small volume of ether and n-hexane to give 4-[(3-isopropyl-4-isopropoxyphenyl)carboxamide]benzoic acid (1.9 g).

MS (El): m/z 341 ($M^+$), 205, 163

PREPARATION EXAMPLE 2

In the same manner as preparation example 1,3-isopropyl-4-isopropoxybenzoic acid was condensed with ethyl 4-aminosalicylate and the resulting ester was subjected to a hydrolization to give 3-hydroxy-4-[(3-isopropyl-4 -isopropoxyphenyl)carboxamide]benzoic acid.

MS (El): m/z 357 ($M^+$), 313, 205, 163

Experiment 1: Measurement of activity of alkaline-phosphatase

MC3T3-E1 cells, established cell line of osteoblastic cell, were subcultured in α-MEM culture medium containing 10% fetal bovine serum placed in an incubator under 5% $CO_2$ atmosphere at 37° C. The MC3T3-E1 cells described above were seeded into each well of a 24-well plate containing 1 ml of culture medium up to $1 \cdot 10^4$ cells/well and cultured for 3 days in the incubator. The cultured medium was removed and then 1 ml of α-MEM culture medium containing each test compound at concentrations of from $10^{-5}$ to $10^{-12}$ M and 0.3% bovine serum albumin was added and cultured for additional 2 days. Then, the cultured medium was removed and the cells were added with 200 μml of 0.2% Nonidet P-40 (Nakarai Kagaku Yakuhin Co.) solution containing 1 mM magnesium chloride and incubated for 1 hour at 37° C. The extract solution was transferred into a test tube and centrifuged, and then 100 μl of the resulting supernatant solution obtained by the centrifugation was added to 100 μl of a substrate solution (0.2M glycine buffer (pH 10.4), 20 mM zinc chloride, 20 mM magnesium chloride, 20 mM p-nitrophenyl phosphate), which was preliminarily warmed for 3 minutes at 37° C. The mixture was allowed to react for 120 minutes at 37° C. The reaction was stopped by adding 1.5 ml of 0.15M sodium hydroxide solution and alkaline phosphatase activity was determined by measuring absorbance at 420 nm using a spectrophotometer.

Minimum effective concentrations of the compounds which induce significant increases of alkaline-phosphatase activities as compared with a compound-free reference are set out in Table 1. By t-test evaluation of the significant increases, p values of less than 0.01 were obtained.

TABLE 1

| Test Compound | Minimum Effective Concentration (M) |
|---|---|
| Etretinate | $10^{-7}$ |
| Re 80 | $10^{-10}$ |
| Fv80 | $10^{-10}$ |
| Am580 | $10^{-10}$ |
| Am80 | $10^{-9}$ |
| R300 | $10^{-9}$ |
| Az68 | $10^{-9}$ |
| Ch55 | $10^{-10}$ |
| Ep80 | $10^{-9}$ |
| Fv180 | $10^{-9}$ |
| Am685 | $10^{-9}$ |
| Am589 | $10^{-9}$ |
| Am689 | $10^{-8}$ |

Chemical structures of the compounds used in the above Experiment 1 are set out below:

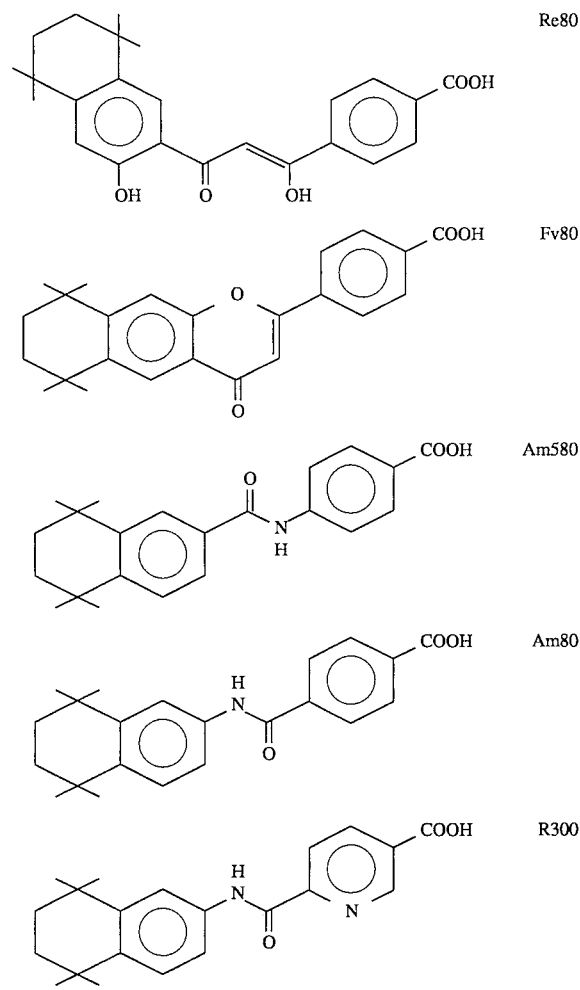

-continued

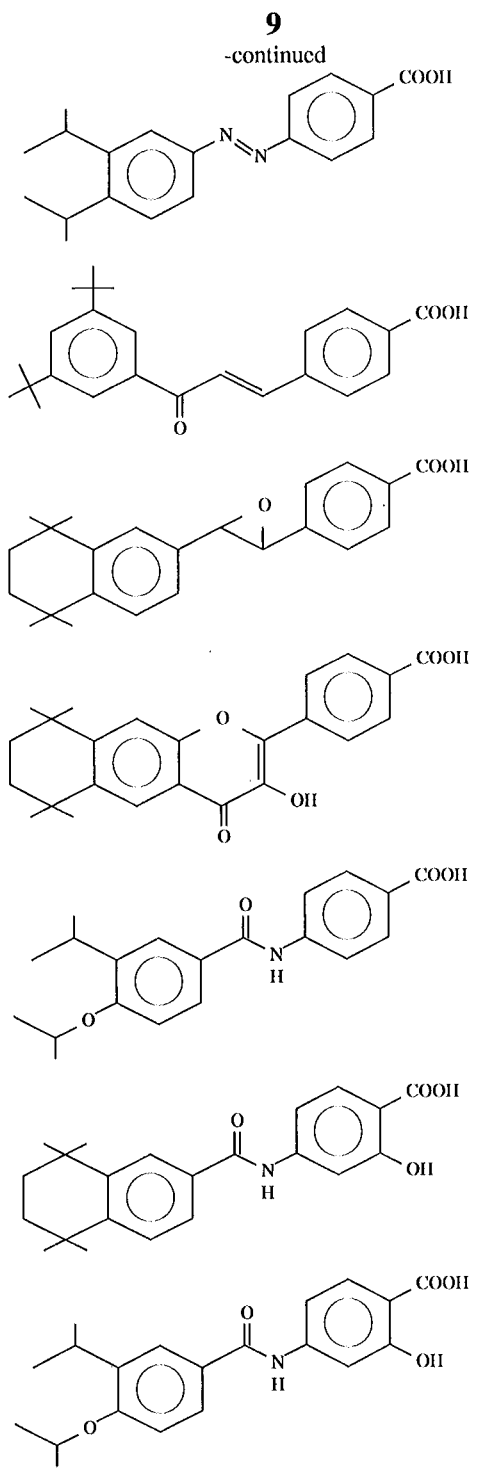

It is apparent from the results summarized above that the compounds Re80 and Am580 contained in the anti-osteopathic composition of the present invention have remarkable effects on osteogenesis of osteoblasts. It is also apparent that these effects are significantly remarkable as compared with etretinate and that the compounds contained in the anti-osteopathic composition of the present invention have extremely high activities.

Experiment 2: Effects on a model of bone atrophy by immobilization.

Models of bone atrophy by immobilization were prepared by brachial neurectomy in the left axia of 6-week old male SD rats anesthetized with pentobarbital. After two weeks from the neurectomy, a suspension of retinoic acid, etretinate or Am580 contained in the anti-osteopathic composition of the present invention in a solution of 0.5% CMC was administered orally to a group of rat consisting of 6 treated rats once a day for two weeks at a daily dose of 0.01 mg/kg or 0.1 mg/kg. The same volume of 0.5% CMC solution was administered in a similar manner to a solvent-administered reference group. After completion of successive administration for 2 weeks, left radius (the side of neurectomy) and right radius (the side of non-neurectomy) were removed. After an alcoholic dehydration and defatting, the bones were dried at 160° C. for 6 hours to measure their dry weights. The bones were then heated for ashing at 600° C. for 24 hours to measure the weights of ash content. As a non-treated reference group, left and right radiuses and the bones were treated in the same manner to measure bone dry weight and ash content. Efficacy of each compound was evaluated by t-test between the measurements of the group administered with the test compound and those of the two reference groups. The results are summarized in Table 2.

TABLE 2

| Compound | Dry Weight of Radius (mg) | | Ash Weight of Radius (mg) | |
|---|---|---|---|---|
| | Left[1] | Right[2] | Left[1] | Right[2] |
| Ref.[3] | 109.3 ± 5.3 (100) | 107.7 ± 2.6 (100) | 76.5 ± 3.8 (100) | 75.1 ± 2.3 (100) |
| Ref.[4] | 94.1 ± 1.8A (86.1) | 108.3 ± 2.0 (100.6) | 64.9 ± 1.0A (84.8) | 75.1 ± 1.4 (100.0) |
| Am580 (0.01 mg/kg) | 99.5 ± 6.2a (91.0) | 111.2 ± 6.0 (103.2) | 69.3 ± 5.0a (90.6) | 77.0 ± 4.3 (102.5) |
| Am580 | 101.5 ± 4.1a,b | 118.2 ± 3.5A,B | 70.1 ± 2.3A,B | 82.1 ± 2.4A,B |

TABLE 2-continued

| Compound | Dry Weight of Radius (mg) | | Ash Weight of Radius (mg) | |
| --- | --- | --- | --- | --- |
| | Left[1] | Right[2] | Left[1] | Right[2] |
| (0.1 mg/kg) | (92.9) | (109.7) | (91.6) | (109.3) |
| Ref.[3] | 118.3 ± 6.2 | 118.1 ± 4.8 | 82.7 ± 3.4 | 82.5 ± 3.1 |
| | (100) | (100) | (100) | (100) |
| Ref.[4] | 105.2 ± 4.4A | 121.4 ± 2.8 | 72.9 ± 3.0A | 84.5 ± 2.1 |
| | (88.9) | (102.8) | (88.1) | (102.4) |
| Retinoic Acid | 100.1 ± 4.7A | 114.9 ± 6.3b | 69.0 ± 3.0Ab | 80.1 ± 4.4 |
| (0.01 mg/kg) | (84.6) | (97.3) | (83.4) | (97.1) |
| Retinoic Acid | 100.6 ± 4.2A | 122.2 ± 4.1 | 73.4 ± 2.7A | 84.8 ± 2.4 |
| (0.1 mg/kg) | (85.0) | (103.5) | (88.8) | (102.8) |
| Ref.[3] | 112.6 ± 3.7 | 111.6 ± 3.6 | 80.3 ± 2.6 | 79.6 ± 2.8 |
| | (100) | (100) | (100) | (100) |
| Ref.[4] | 97.7 ± 12.8a | 111.0 ± 11.6 | 68.6 ± 9.1a | 78.1 ± 7.8 |
| | (86.8) | (99.5) | (85.4) | (98.1) |
| Etretinate | 97.8 ± 4.7A | 113.6 ± 7.8 | 68.1 ± 3.5A | 79.6 ± 5.6 |
| (0.01 mg/kg) | (86.9) | (101.8) | (84.8) | (100.0) |
| Etretinate | 100.9 ± 2.4A | 115.9 ± 4.3 | 69.8 ± 1.6A | 80.6 ± 2.8 |
| (0.1 mg/kg) | (89.6) | (103.9) | (86.9) | (101.3) |

[1]The side of neurectomy
[2]The side of non-neurectomy
[3]Non-treated Reference
[4]Solvent-administered Reference
A,a, A significant difference was observed in comparison with non-treating reference.
a = p < 0.05, A = p < 0.01
B,b, A significant difference was observed in comparison with solvent-administered reference.
b = p < 0.05, B = p < 0.01
( ) Relative value where the values of non-treating reference equals to 100.

By brachial neurectomy, the dry weights and ash weight of the radius in the side of neurectomy were significantly decreased. However, no decrease was found in the side of non-neurectomy, and accordingly, no effect of the neurectomy was observed in the side of non-neurectomy. It was found that Am580, one of the compounds contained in the anti-osteopathic composition of the present invention, has potency of inhibitory effect on decreases of dry weight and ash weight of radius at the dose of 0.01 mg/kg, although the differences were insignificant, and it remarkably inhibits the decrease at the dose of 0.1 mg/kg. In the side of non-neurectomy, significant increases of dry weights and ash weights of radiuses were observed in the group administered with 0.1 mg/kg of Am580 as compared to non-treated and solvent administered reference groups, which is evidence of an enhancing activity on osteogenesis. In the group administered with etretinate, it was revealed that etretinate has a potency of inhibiting the decrease of dry weight and ash weight of the radius in the side of neurectomy and it also has a potency of inducing the weight increase of the bones in the side of non-neurectomy at the dose of 0.1 mg/kg, although the differences were insignificant. Retinoic acid did not have significant effect in this experimental system.

The above-described results clearly show that Am580, one of the compounds contained in the anti-osteopathic composition of the present invention, exhibits a remarkable inhibitory activity on the decrease of bone amount and an enhancing activity on osteogenesis. The activities are unexpectedly remarkable as compared with those of retinoic acid and etretinate, and therefore, it is apparent that the anti-osteopathic composition according to the present invention is useful.

We claim:

1. A method for treatment of a bone disease which comprises a step of administering to a patient in recognized need thereof, an anti-osteopathic composition comprising as an active ingredient a compound represented by the following formula (I):

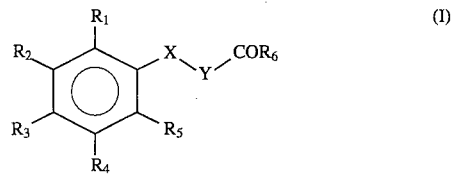

wherein $R_1$, $R_4$, and $R_5$ are hydrogen atoms; $R_2$ and $R_3$ independently represent a $C_1$–$C_4$ alkyl group or a $C_1$–$C_4$ alkoxy group or $R_2$ and $R_3$ may combine to form a 5- or 6-membered cycloalkyl ring together with carbon atoms to which they are bonded, wherein the cycloalkyl ring can be substituted with one or more $C_1$–$C_2$ alkyl groups; $R_6$ represents hydroxy or a $C_1$–$C_2$ alkoxy group; X is selected from the group consisting of —NH—CO— and —CO—NH—; and Y is selected from the group consisting of:

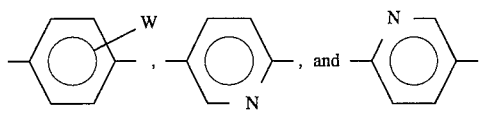

wherein W is hydrogen or hydroxy, or a pharmaceutically acceptable salt thereof.

* * * * *